United States Patent [19]

Wade et al.

[11] 4,228,186
[45] Oct. 14, 1980

[54] METHOD FOR THE CONTROL OF MANURE-BREEDING INSECTS

[75] Inventors: Lisby L. Wade, Lake Jackson, Tex.; Donald L. Clarke, Bay City, Mich.; Jack P. Arrington, Clayton, Calif.

[73] Assignee: The Dow Chemical Company, Midland, Mich.

[21] Appl. No.: 965,542

[22] Filed: Dec. 1, 1978

[51] Int. Cl.$^2$ .......................... A01N 9/20; A01N 9/24; C07C 119/00; C07C 131/00
[52] U.S. Cl. .................................. 424/327; 260/566 B
[58] Field of Search ..................... 424/327; 260/566 B

[56] References Cited

U.S. PATENT DOCUMENTS

| | | | |
|---|---|---|---|
| 3,305,347 | 2/1967 | Minieri | 424/327 |
| 3,839,445 | 10/1974 | Boesch | 424/327 |
| 3,847,987 | 11/1974 | Boesch | 260/566 B |
| 3,917,849 | 11/1975 | Boesch | 424/327 |
| 4,015,014 | 3/1977 | Vatne et al. | 424/327 |
| 4,017,540 | 4/1977 | Kaugars et al. | 260/566 B |
| 4,093,656 | 6/1978 | Schimann et al. | 260/566 B |

FOREIGN PATENT DOCUMENTS 750471  6/1956  United Kingdom ..................... 424/327

OTHER PUBLICATIONS

Ulrich, "The Chemistry of Imidoyl Halides", Plenum Press, N.Y. (1968) Chap. 7, pp. 180, 190, 191, 192.
Chem. Abst. 66 85600(f)(1967) - Minieri.

Primary Examiner—Douglas W. Robinson
Attorney, Agent, or Firm—S. Preston Jones; Ronald G. Brookens

[57] ABSTRACT

Manure-breeding insects are controlled by contacting the manure with an insecticidally-effective amount of 2,4-dichloro-N-((chloro-2,4-dichlorophenyl)methylene)benzene carbonhydrazonoyl chloride which corresponds to the formula

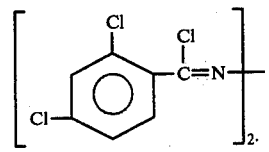

5 Claims, No Drawings

METHOD FOR THE CONTROL OF MANURE-BREEDING INSECTS

BACKGROUND OF THE INVENTION

The present invention is directed to the compound 2,4-dichloro-N-((chloro-2,4-dichlorophenyl)methylene)benzene carbonhydrazonoyl chloride, its preparation and its use in animal husbandry and in particular, its use in the control of manure-breeding insects. These insects include flies which are known to be vectors in the transmission of various animal diseases.

Present control methods consist of sanitation, application of insecticides at regular intervals to control larvae or adults, bait applications, or in the case of chicken houses, even the use of flame throwers at night to kill adults resting on the ceilings and walls.

The present invention is also concerned with the use of an insecticide which can be orally administered to a warm-blooded animal and which will pass, essentially unchanged as to its insecticidal properties, through the animal's digestive system and be eliminated as a part of the animal's solid waste, i.e. manure.

The present invention is further concerned with the control of manure-breeding insects by spraying or otherwise contacting manure with an insecticide capable of controlling manure-breeding insecticides.

SUMMARY OF THE PRESENT INVENTION

The present invention is directed to a method for controlling manure-breeding insects, by contacting manure with an insecticidally-effective amount of 2,4-dichloro-N-((chloro-2,4-dichlorophenyl)methylene)-benzene carbohydrazonoyl chloride which corresponds to the formula

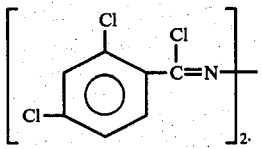

The active compound of the present invention which is utilized in the present method is highly effective in controlling manure-breeding insects such as houseflies, faceflies and hornflies. While the active compound is quite effective when sprayed or otherwise admixed with the manure, this compound has also been found to be useful as a "feed-thru". In this latter procedure, the compound is orally administered to the animal and the compound retains its insecticidal properties after it passes through the digestive system of the treated animal. The compound when acting as a "feed-thru" mixes directly in the animal's solid waste (manure) during the digestive processes, requiring no additional work in controlling the manure-breeding insects.

In the present specification and claims, the phrase "contacting manure" and equivalent phrases thereof are employed to refer to contacting the manure (solid animal waste) outside the animal with the active material by employing techniques such as spraying, blending, and the like techniques as well as contacting manure in the animal prior to its excretion, particularly by oral administration of the active material to the animal for action in the animal as a feed-thru material.

For use as a feed-thru, the active compound can be administered to the warm-blooded animals in admixture with their feed or drinking water. Furthermore, the active compound can be administered in the form of tablets, pills, capsules or the like. The active compound can also be admixed with pharmaceutically-acceptable carriers for use in animals, however, they are usually used as a component in the animal feed or drinking water.

The insecticidally-effective dosage desirable for effective use of preparations containing the active compound will naturally depend on various factors such as the form of preparation and the insect which must be controlled. It is only necessary that the compound be orally administered in a sufficient amount so as to make possible the application of an insecticidally-effective or inactivating dosage. Generally, the active compound can be orally administered to a warm-blooded animal, especially a ruminant, at a daily dosage of from about 0.25 to about 10 milligrams of active compound per kilogram of animal body weight.

When administered to poultry, an effective dosage rate will generally range from about 5 parts to about 50 parts of active compound per million parts of poultry feed.

The active compound can be effectively administered to warm-blooded animals, especially ruminants, dogs, horses, swine and poultry.

For use in direct applications to the manure, the active compound can be formulated with adjuvants into various forms, such as emulsifiable concentrates, wettable powders, dusts, oil sprays and the like. The adjuvant employed can be any one of a plurality of materials including aromatic solvents, petroleum distillates or other liquid carriers, surface-active dispersing agents, light absorbers and finely divided carrier solids.

The exact concentration of the active compound in composition thereof with an adjuvant therefor can vary; it is only necessary that the active compound be present in a sufficient amount so as to make possible the application of an insecticidally-effective dosage to the manure. Generally, for practical applications, the active compound can be applied to the manure in compositions containing from 0.001 percent to about 98 percent by weight of the active compound.

The present invention also comprehends the employment of compositions comprising the active compound, an adjuvant, and one or more other biologically active material such as, insecticides, fungicides, miticides, and the like.

EXAMPLES

The examples which follow should not be construed as limitations upon the overall scope of the invention.

EXAMPLE 1

A cattle feed premix containing 1.005 grams of 2,4-dichloro-N-((chloro-2,4-dichlorophenyl)methylene)-benzene carbohydrazonoyl chloride was mixed into a complete cattle ration to give a total of 500 grams of completed feed. This feed was sub-divided into 100 gram samples, each containing 0.201 grams of the active compound, as the sole insecticide.

A calf weighing 201 kilograms was fed each day for 5 days, a regular feed which had been top-dressed with one of the above 100 gram samples. The active compound was present in the feed in the amount of 0.201 grams (201 mg). The feeding was observed to assure that all of the feed had been consumed.

On the fourth, fifth and sixth day of the test, manure samples were collected from the treated animal and frozen to kill any wild insect larvae that may have been present. The samples were thawed and were seeded with eggs from colony strains of hornflies. Control samples of manure were also similarly seeded at that time. The samples were incubated at 80° F. for a period of time sufficient to allow the eggs to hatch (14 days).

The percent control was determined by counting the number of normal adult flies that hatched from the treated samples and comparing this figure with the number of flies that hatched from the untreated (control) samples. It was determined that there was, in the treated samples, a 94% control of hornflies.

EXAMPLE 2

The compound 2,4-dichloro-N-((chloro-2,4-dichlorophenyl)methylene)benzene carbohydrazonoyl chloride was added to a commercial chicken feed in an amount sufficient to provide 500 parts of the compound per million parts of feed.

The feed was fed to caged chickens of like age for 7 days. The chicken droppings were allowed to collect under the cages for 5 days and were allowed to become infected with the normally occuring populations of flies (i.e. houseflies). Nine-ounce sample cups were filled with the droppings and at the same time cups were filled with droppings from chickens of the same age which had been fed the same feed containing no insecticide, to serve as controls. The cups were allowed to incubate for three weeks in separate cages until all flies had hatched and died. The dead flies were counted to determine the number of flies which hatched and compared with the number of flies which hatched from the control. It was determined that there was, in the treated samples, a 100% control of houseflies.

EXAMPLE 3

Manure samples from cattle were collected and frozen to kill any wild insect larvae that may have been present. The samples were thawed and mixed with an aqueous dispersion of 2,4-dichloro-N-((chloro-2,4-dichlorophenyl)methylene)benzene carbohydrazonoyl chloride to provide a sample containing 10 parts of the compound per million parts of the ultimate mixture. The treated samples and samples containing no toxicant, to serve as controls, were each seeded with ~200 housefly eggs. The samples were incubated at 80° F. for 15 days to provide sufficient time for the eggs to hatch.

The percent control was determined by counting the number of normal adult flies that hatched from the treated samples and comparing this figure with the number of flies that hatched from the untreated (control) samples. It was determined that there was, in the treated samples, a 100% control of houseflies.

PREPARATION OF THE ACTIVE COMPOUND

The active compound utilized in the present method can be prepared by the reaction of 1,2,-di-(2,4-dichlorobenzoyl)hydrazine with excess phosphorous pentachloride in the presence of phosphorous pentoxide with or without a solvent such as chlorobenzene, dichlorobenzene or phosphorous oxychloride.

In carrying out the reaction, the phosphorous pentachloride and phosphorous pentoxide and solvent are heated, at atmospheric pressure, to reflux and the hydrazine reactant added. The reaction is conducted under reflux conditions and the reaction is usually complete in from ~15 minutes to ~one hour depending on the specific solvent.

Following the completion of the reaction, the product is recovered and purified by conventional separatory techniques of solvent extraction, water washing, filtration and recrystallization.

EXAMPLE 2,4-Dichloro-N-((chloro-2,4-dichlorophenyl)methylene)benzene carbohydrazonoyl chloride

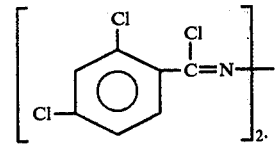

Into a 2-liter, 3-necked flask were placed 60 grams (g) of phosphorous pentachloride, 0.2 g of phosphorous pentoxide and 60 cubic centimeters (cc) of chlorobenzene. This mixture was heated to reflux, with stirring. To this mixture was added over ~one hour, 58 g (0.15 m) of 1,2-di-(2,4-dichlorobenzoyl)hydrazine. After the addition was complete, the mixture was refluxed for an additional one-half hour. The reaction mixture was cooled and poured, with vigorous stirring, into one liter of ice water. The crude 2,4-dichloro-N-((chloro-2,4-dichlorophenyl)methylene)benzene carbohydrazonoyl chloride product was extracted twice with 750 cc portions of methylene chloride. The organic extracts were combined, washed with aqueous sodium bicarbonate solution and dried over anhydrous magnesium sulfate. The solution was filtered to remove insolubles and the filtrate concentrated under reduced pressure. The residue was taken up in 400 cc of hot ethyl acetate and allowed to cool. The solution was filtered to remove insolubles and the filtrate concentrated. The residue was recrystallized from hexane to give 13.5 grams (21 percent of theoretical) of the product. The product melted at 96.5°–98° C. and upon analysis was found to have carbon, hydrogen and nitrogen contents of 40.65, 1.58 and 6.99 percent, respectively as compared with the theoretical contents of 40.53, 1.46 and 6.75 percent, respectively, calculated for the above named compound.

What is claimed is:

1. 2,4-Dichloro-N-((chloro-2,4-dichlorophenyl)methylene)benzene carbonhydrazonoyl.

2. A composition useful for controlling manure-breeding insects which comprises an insecticidally effective amount of 2,4-dichloro-N-((chloro-2,4-dichlorophenyl)methylene)benzene carbonhydrazonoyl chloride and an inert adjuvant therefor.

3. A method for controlling manure-breeding insects which comprises contacting manure with an insecticidally effective amount of a composition comprising 2,4-dichloro-N-((chloro-2,4-dichlorophenyl)methylene)benzene carbonhydrazonoyl chloride and an inert adjuvant therefor.

4. The method as defined in claim 3 wherein excreted manure is contacted with the composition.

5. The method of controlling manure-breeding insects which comprises orally administrating to an animal an insecticidally effective amount of a composition comprising 2,4-dichloro-N-((chloro-2,4-dichlorophenyl)methylene)benzene carbonhydrazonoyl chloride and an inert adjuvant therefor.

* * * * *